US009188997B2

(12) United States Patent
Mohan et al.

(10) Patent No.: US 9,188,997 B2
(45) Date of Patent: Nov. 17, 2015

(54) CONFIGURATION FREE AND DEVICE BEHAVIOR UNAWARE WIRELESS SWITCH

(71) Applicants: Tanuj Mohan, Mountain View, CA (US); Omkar Prabhu, Sunnyvale, CA (US); Saurabh Gupta, Sunnyvale, CA (US)

(72) Inventors: Tanuj Mohan, Mountain View, CA (US); Omkar Prabhu, Sunnyvale, CA (US); Saurabh Gupta, Sunnyvale, CA (US)

(73) Assignee: enLighted, Inc., Sunnyvale, CA (US)

( * ) Notice: Subject to any disclaimer, the term of this patent is extended or adjusted under 35 U.S.C. 154(b) by 182 days.

(21) Appl. No.: 14/025,959

(22) Filed: Sep. 13, 2013

(65) Prior Publication Data
US 2014/0265927 A1 Sep. 18, 2014

Related U.S. Application Data

(60) Provisional application No. 61/789,585, filed on Mar. 15, 2013.

(51) Int. Cl.
G05D 27/02 (2006.01)
H05B 37/02 (2006.01)

(52) U.S. Cl.
CPC ............ G05D 27/02 (2013.01); H05B 37/0245 (2013.01)

(58) Field of Classification Search
CPC ............... G05D 27/02; H05B 37/0245; H05B 37/0254; H05B 37/0272; H05B 37/029
See application file for complete search history.

(56) References Cited

U.S. PATENT DOCUMENTS

| | | | |
|---|---|---|---|
| 5,101,141 A | 3/1992 | Warner et al. | |
| 5,179,324 A | 1/1993 | Audbert | |
| 5,191,265 A | 3/1993 | D'Aleo et al. | |
| 5,283,516 A | 2/1994 | Lohoff | |
| 5,812,422 A | 9/1998 | Lyons | |
| 6,057,654 A | 5/2000 | Cousy et al. | |
| 6,188,181 B1 | 2/2001 | Sinha et al. | |
| 6,342,994 B1 | 1/2002 | Cousy et al. | |
| 6,548,967 B1 | 4/2003 | Dowling et al. | |
| 7,309,985 B2 | 12/2007 | Eggers et al. | |
| 7,348,736 B2 | 3/2008 | Piepgras et al. | |
| 7,382,271 B2 | 6/2008 | McFarland | |
| 7,437,596 B2 | 10/2008 | McFarland | |
| 7,550,931 B2 | 6/2009 | Lys et al. | |
| 7,566,137 B2 | 7/2009 | Veskovic | |

(Continued)

FOREIGN PATENT DOCUMENTS

WO WO2012109696 8/2012

OTHER PUBLICATIONS

PCT Notification of Transmittal of the International Search Report and the Written Opinion of the International Searching Authority, or the Declaration, International Application No. PCT/US2014/022154, Dated Jun. 26, 2014.

Primary Examiner — Jung Kim
(74) Attorney, Agent, or Firm — Brian R. Short

(57) ABSTRACT

Apparatuses, methods and systems for controlling lighting, an environment factor, or security of a structure are discloses. A lighting control system includes a plurality of lighting devices, a central server and a switch. The central server communicates with each of the plurality of lighting devices, and controls an operating configuration of each of the lighting devices. The switch communicates with at least some of the plurality of lighting devices, wherein the communication includes information, and wherein the at least some of the plurality of lighting devices respond to the information based on the operating configuration of the at least some of the plurality of lighting devices.

21 Claims, 6 Drawing Sheets

(56) References Cited

U.S. PATENT DOCUMENTS

| | | |
|---|---|---|
| 7,623,042 B2 | 11/2009 | Huizenga |
| 7,792,956 B2 | 9/2010 | Choong et al. |
| 7,925,384 B2 | 4/2011 | Huizenga et al. |
| 8,368,310 B1 | 2/2013 | Roosli |
| 2002/0048169 A1* | 4/2002 | Dowling et al. ............ 362/234 |
| 2004/0002792 A1 | 1/2004 | Hoffknecht |
| 2005/0169643 A1 | 8/2005 | Franklin et al. |
| 2006/0275040 A1 | 12/2006 | Franklin |
| 2007/0057807 A1* | 3/2007 | Walters et al. ............. 340/825 |
| 2007/0061050 A1 | 3/2007 | Hoffknecht |
| 2007/0086128 A1 | 4/2007 | Lane et al. |
| 2007/0215794 A1 | 9/2007 | Cernasov et al. |
| 2008/0185597 A1 | 8/2008 | Wu |
| 2008/0244104 A1 | 10/2008 | Clemente |
| 2008/0265796 A1 | 10/2008 | Null |
| 2008/0265799 A1* | 10/2008 | Sibert ......................... 315/292 |
| 2009/0026966 A1 | 1/2009 | Budde et al. |
| 2009/0085500 A1* | 4/2009 | Zampini et al. ............. 315/297 |
| 2009/0179596 A1 | 7/2009 | Willaert et al. |
| 2009/0195161 A1 | 8/2009 | Lane et al. |
| 2010/0034386 A1 | 2/2010 | Choong et al. |
| 2010/0135186 A1 | 6/2010 | Choong et al. |
| 2010/0244706 A1* | 9/2010 | Steiner et al. ............... 315/149 |
| 2010/0264846 A1 | 10/2010 | Chemal et al. |
| 2010/0270933 A1 | 10/2010 | Chemal et al. |
| 2010/0295482 A1 | 11/2010 | Chemal et al. |
| 2010/0301777 A1 | 12/2010 | Kraemer |
| 2011/0031897 A1 | 2/2011 | Henig et al. |
| 2012/0074852 A1 | 3/2012 | Delnoij |
| 2012/0086363 A1 | 4/2012 | Golding |
| 2012/0130544 A1* | 5/2012 | Mohan et al. ............... 700/275 |

* cited by examiner

US 9,188,997 B2

CONFIGURATION FREE AND DEVICE BEHAVIOR UNAWARE WIRELESS SWITCH

RELATED APPLICATIONS

This patent application claims priority to U.S. Provisional Patent Application Ser. No. 61/789,585, filed Mar. 15, 2013, which is herein incorporated by reference.

FIELD OF THE EMBODIMENTS

The described embodiments relate generally to environmental control. More particularly, the described embodiments relate to apparatuses, methods and systems of a configuration free and device behavior unaware wireless switch, and control of environmental fixtures by the wireless switch.

BACKGROUND

Typical wireless switches that are battery powered have to optimize between battery-life, functionality, flexibility and security. Existing garage door openers, wireless remotes are either paired at the factory with knowledge and shared secrets of the device they are controlling losing flexibility or are generic, thereby compromising security. For example, one remote control wireless switch from the same manufacturer can affect all controlled devices from that manufacturer.

The battery life limits these devices from being turned on all the time. It is desirable to extend the battery life by only waking up (activating) the device (wireless switch) sending control messages and not having to wait for a response before going to sleep to conserve battery power.

Wireless switches that control scenes typically go through extensive pre-configuration and switch customization. The switches store configuration information that is button dependent. These switches also require two-way communication to keep the devices under control synchronized.

It is desirable to have methods, systems and apparatuses for a wireless switch, and control of devices (such as, lighting fixtures) by the wireless switch. It is also desirable to upgrade the firmware on these devices to fix bugs in deployed switches and leverage improved security capabilities as standards and techniques improve.

SUMMARY

An embodiment includes lighting control system. The lighting control system includes a plurality of lighting devices, a central server and a switch. The central server communicates with each of the plurality of lighting devices, and controls an operating configuration of each of the lighting devices. The switch communicates with at least some of the plurality of lighting devices, wherein the communication includes information, and wherein the at least some of the plurality of lighting devices respond to the information based on the operating configuration of the at least some of the plurality of lighting devices.

Another embodiment includes method of controlling lighting of a structure. The method includes communicating, by a central server, with each of a plurality of lighting devices, wherein the communication provides control of an operating configuration of each of the lighting devices, and communicating, by a switch, with at least some of the plurality of lighting devices, wherein the communication includes information, and wherein the at least some of the plurality of lighting devices respond to the information based on the operating configuration of the at least some of the plurality of lighting devices.

Another embodiment includes an environmental control system. The environmental control system includes a plurality of environmental control devices, a central server, and a switch. The central server communicates with each of the plurality of environmental control devices, and controls an operating configuration of each of the environmental control devices. The switch communicates with at least some of the plurality of environmental control devices, wherein the communication includes information, and wherein the at least some of the plurality of environmental control devices respond to the information based on the operating configuration of the at least some of the plurality of environmental control devices.

DETAILED DESCRIPTION

The described embodiments are embodied in an apparatuses, systems and methods of a configuration free and scene unaware (wired or wireless) switch, and control of building fixtures by the switch. For lighting devices, the different settings of the lighting devices can be referred to as "scenes". For at least some embodiments, the switch merely sends messages (for example, through wired connections or through a wireless broadcast) to the lighting devices. The switch is not aware of what the setting (scene) the messages correspond to—that is, the switch is scene unaware. The lighting devices respond to the messages as determined by an operating configuration of each lighting device. That is, each lighting device goes to an operating scene as determined by the operating configuration of the lighting device.

Figure 1:
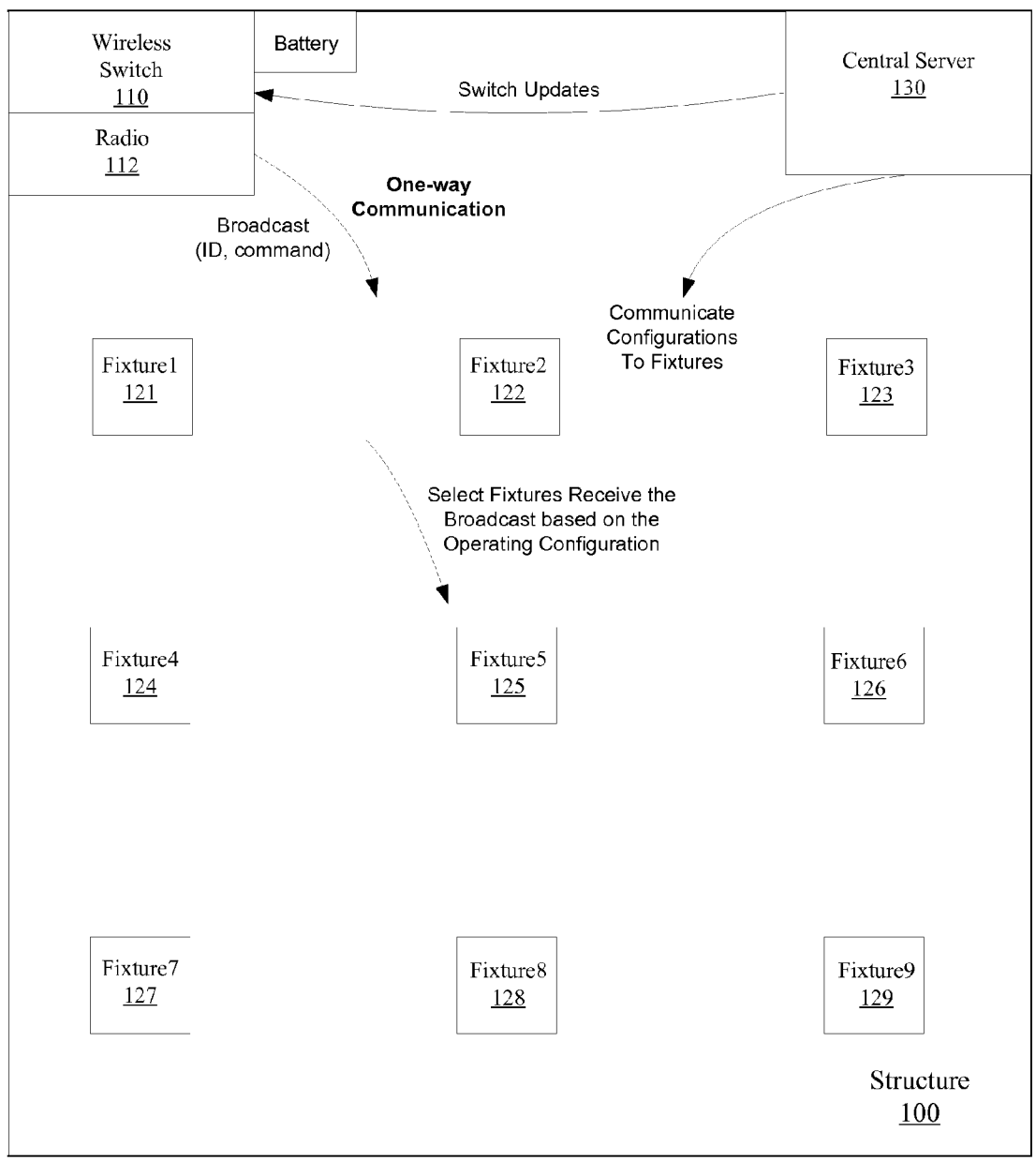
FIG. 1 shows a lighting system that includes a wireless switch, a plurality of lighting fixtures, and a central controller, according to an embodiment.

FIG. 1 shows a lighting system that includes a wireless switch 110, a plurality of fixtures 121-129, and a central controller 130, according to an embodiment. While shown as a wireless switch, it is to be understood that for at least some embodiment, the switch includes a wired switch that includes wired electrical connections to the plurality of fixtures 121-129. For at least some embodiments, the wireless switch wirelessly broadcast at least an ID (such as, an identification of the switch 110) and a command. It is to be noted that for an embodiment the broadcast is a one-way communication, and therefore, does not require the wireless switch to include power-consuming wireless receiver circuitry. For an embodiment, the command includes an indication of a button on the switch that has been pressed or otherwise activated by a user.

While only a single switch 110 is shown in FIG. 1, clearly additional switches can be located within a structure 100. For an embodiment, each of the wireless switches has a unique identification.

As described, for a wireless switch, for an embodiment, the communication includes a wireless broadcast, and the information includes a switch identification, and button activate information. However, if the switch is a wired switch, the identification is not needed, and the information can only include button activate information.

While described as a wireless broadcast, for at least some embodiments, all that is required is that a message be communicated from the switch to the devices. Generally, a broadcast message is a message that is transmitted and received by only a select number of devices. For at least some embodiments, the devices selected to receive the broadcast is determined by the operating configuration of the device. That is, for example, the operating configuration of a device is set such that the device is operable to receive broadcast information from wireless switches having a particular or particular set of identifiers within their broadcasts. For at least some embodiments, the information within the broadcast sets the setting or scene of the device as determined by the operating configuration.

For at least some embodiments, the broadcasts from the wireless switches merely indicated a state of the wireless switch, and the devices react to the broadcasts as determined by the operating configuration of the device.

For at least some embodiments, the operating configuration of each device is set by the central server 130. For an embodiment, the operating configurations adaptively change, for example, dependent on the time of the day, week, month or year. The operating configuration can also adaptively change depending on a security or emergency situation identified within a structure that includes the lighting or environmental control system.

For at least some embodiments, the operating configuration includes a preconfigured set or sets of scenes. For example, a scene for a conference room could include a presentation scene wherein all the lights within the conference room close to a viewing screen dim. Another exemplary scene may include a video conference friendly scene. For at least some embodiments, the operating configuration and/or a scene applies or is maintained as long as there is continuous motion sensed within the space being controlled by the lighting or environmental control system. Continuous motion can be determined by sensing motion of greater than a motion threshold, wherein the time duration between sensing the motion of greater than the motion threshold is continuously less than a time threshold.

For at least some embodiments, the preconfigured scenes include the setting of the light levels of a set of light fixtures. Further, the scene selection determines transition times (that is, transition time from one light level to another) and applicable time (that is, how long the light level is applied) of the settings to the light fixtures. The applicable time can determine when to go back to, for example, a default setting. Further the applicable time can be time-based, motion-based and/or light (sensed) based.

While the described embodiments may state or suggest that the fixtures 121-129 are lighting fixtures or devices, it is to be understood that the fixtures 121-129 can additionally or alternatively be any type of environmental control, such as, heating, air conditioning etc. Additionally, or alternatively, one or more of the fixtures can be a security device.

The broadcast is received by a plurality of the fixtures 121-129. Each of the fixtures 121-129 has previously received a configuration from, for example, the central controller 130. The configuration of each fixture indicates to the fixture what wireless switch (through the receive ID of the switch) the fixture is to respond to, and what command corresponds to what action of the fixture. For example, a wireless broadcast received from a first wireless switch (again, identified through the received ID) that includes a first command can indicate to the fixture to a go to a first configuration setting, and a wireless broadcast received from a second wireless switch (again, identified through the received ID) that includes a second command can indicate to the fixture to a go to another configuration setting.

As stated, for an embodiment, each of the plurality of fixtures receives operating configurations from the central controller (server) 130. For an embodiment, the operating configurations are adaptively controlled or provided by a system user. For an embodiment, the central controller 130 monitors or receives usage of the structure, and adapts the operating configuration accordingly.

Figure 2:
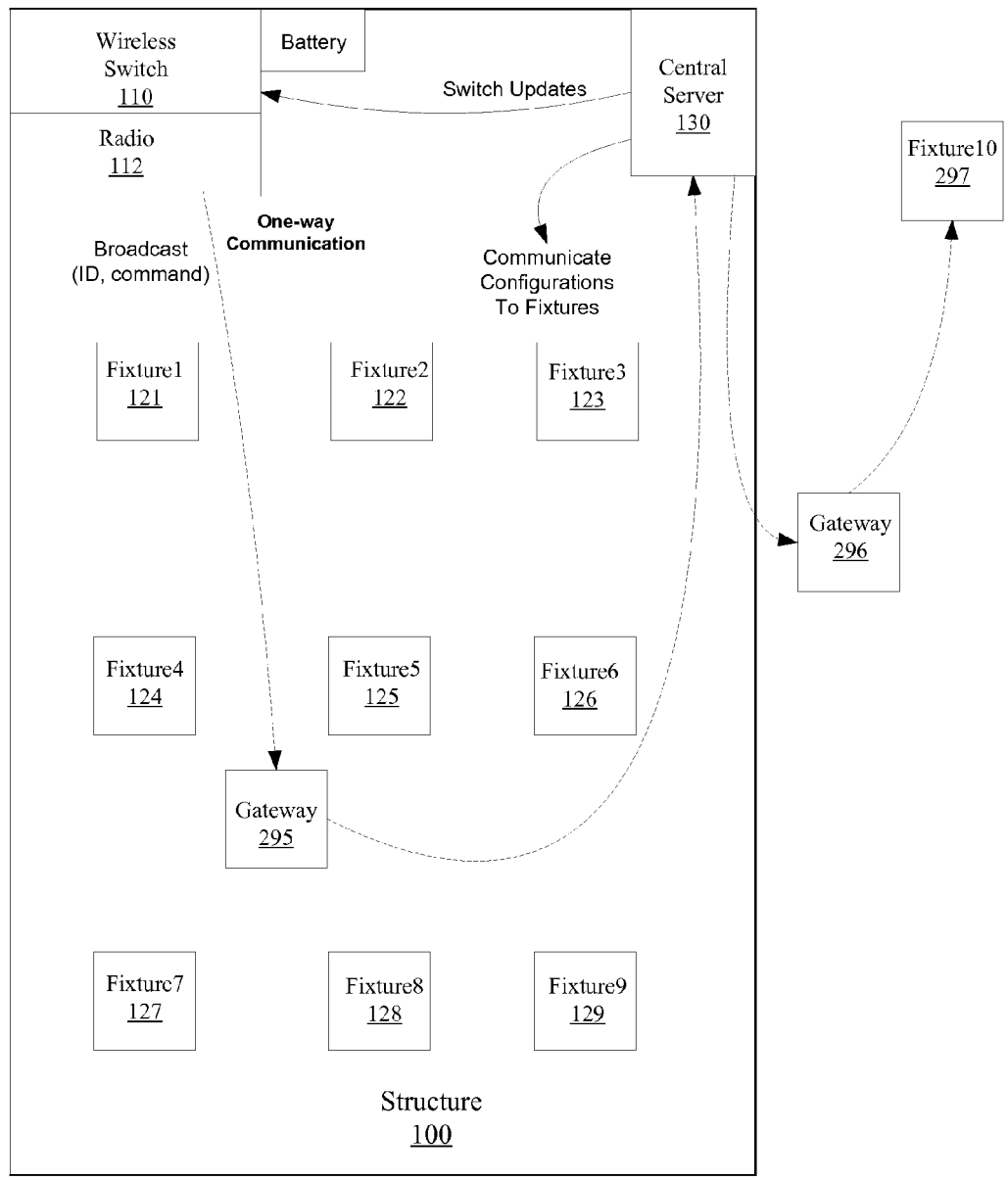
FIG. 2 shows another lighting system that includes a wireless switch, a plurality of lighting fixtures, and a central controller, according to another embodiment.

FIG. 2 shows another lighting system that includes a wireless switch, a plurality of lighting fixtures, and a central controller, according to another embodiment. This embodiment further shows the wireless switch broadcasting (one-way communication) to a gateway 295 directly or via a fixture (such as, fixture 1 121). The gateway 295 propagates the command (for example, button selection of the wireless switch) to the central server 130, which propagates the command to another gateway 296, which propagates the command to a fixture 297. This illustrates that the wireless switch 110 has the capability to communicate with a device (such as, fixture 297) that is outside of the range of the wireless one-way communication (for example, the broadcast) of the wireless switch. The out-of-range device (fixture 297) can be located, for example, on a different floor of the structure 100.

Figure 3:
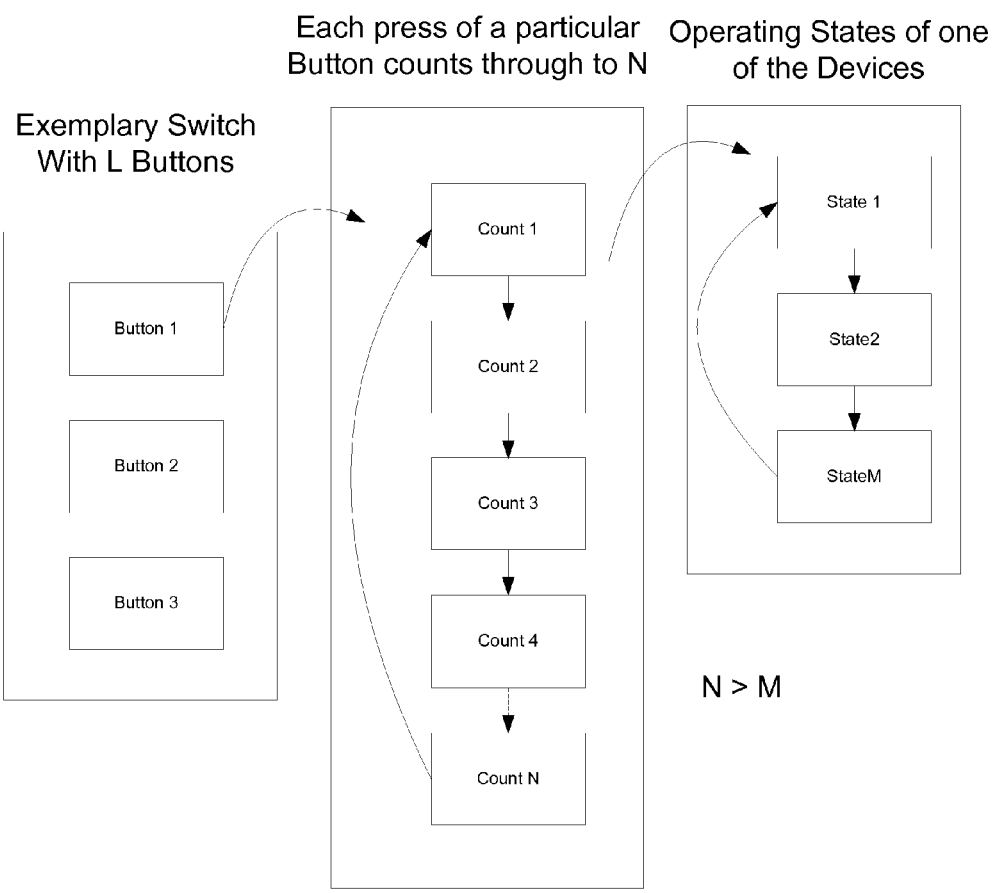
FIG. 3 shows a wireless switch, and shows diagrams of a count of a single button of the wireless switch, and states of one of the plurality of lighting fixtures, according to an embodiment.

FIG. 3 shows a wireless switch (the exemplary switch has 3 buttons), and shows diagrams of a count of a single button (the exemplary button has N counts) of the wireless switch, and states (the exemplary device has M states for the first button) of one of the plurality of lighting fixtures, according to an embodiment. This embodiment ensures that each of the plurality of lighting fixtures is properly synchronized with other lighting fixtures. That is, for an embodiment, the wireless switch merely toggles through operating states as determined, for example, by successive button pushes. The command of the broadcast can include the present state of the wireless switch, and the fixtures can be configured to go to a particular state (operating condition) upon receiving the state information of the wireless switch.

For this embodiment, the button (for example, the first button) of wireless switch has N possible states. For an embodiment, the wireless switch merely includes a counter that increments with each button push. As a result, the switch has no idea of what state it is in. However, activating the button of the switch causes states and/or scenes of the devices to change. Each of the fixtures can determine which of their M states they are to be operating by performing an n1 Mod M calculation, where n1 is the one of the N counts of the counter within the switch, and M is the number of states of the device. Each of the plurality of devices is able to maintain synchronization with each other using this method. Even if a device misses the wireless signals of the next push or activation, the state determination ensures that the devices (that is, multiple devices, wherein the multiple devices are not clock synchronized) react in unison. For example if the 2 scenes are 1) all on and 2) all off, then if half the lights do not get the message and are out of sync with the expected user behavior then every subsequent button push would continue this problem without logic that causes the devices to re-synchronize.

Figure 4:
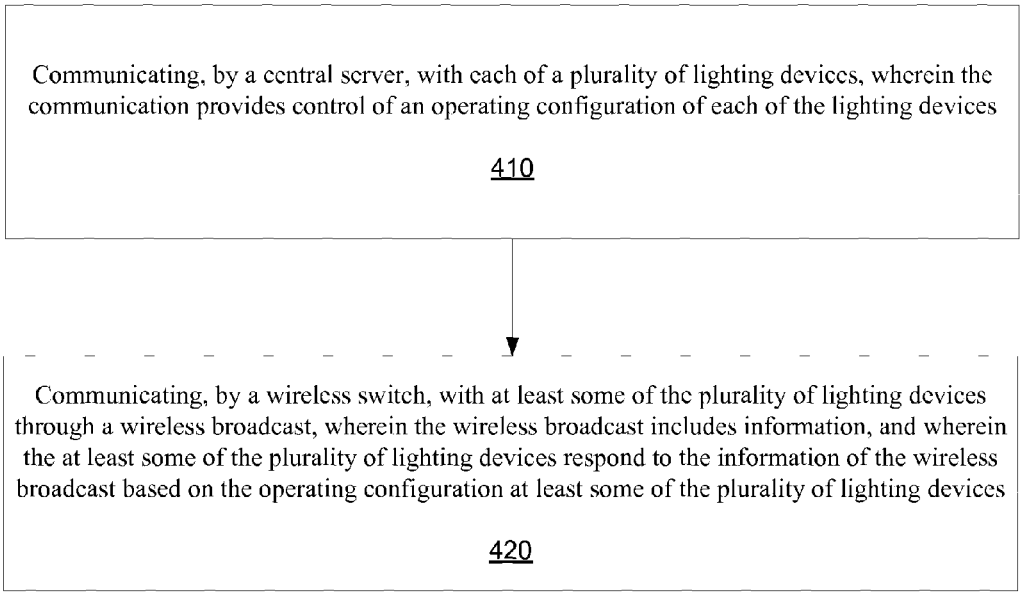
FIG. 4 is a flow chart that includes steps of a method of controlling lighting of a structure, according to an embodiment.

FIG. 4 is a flow chart that includes steps of a method of controlling lighting of a structure, according to an embodiment. A first step 410 includes communicating, by a central server, with each of a plurality of lighting devices, wherein the communication provides control of an operating configuration of each of the lighting devices. A second step 420 includes communicating, by a wireless switch, with at least some of the plurality of lighting devices through a wireless broadcast, wherein the wireless broadcast includes information, and wherein the at least some of the plurality of lighting devices respond to the information of the wireless broadcast based on the operating configuration at least some of the plurality of lighting devices.

While described in the context of lighting devices, it is to be understood that the described embodiments are adaptable to any type of environmental control system. Rather than lighting devices, the environmental control system can include a plurality of environmental control devices. A central server is operative to communicate with each of the plurality of environmental control devices, and controls an operating configuration of each of the environmental control devices. For at least some embodiments, the central server is operative to provide software upgrades to the wireless switch. For at least some embodiments, the software upgrades include software bug fixes and/or communication security enhancements.

Further, an embodiment of the wireless switch communicates with at least some of the plurality of environmental control devices through a wireless broadcast, wherein the wireless broadcast includes information, and wherein the at least some of the plurality of environmental control devices respond to the information of the wireless broadcast based on the operating configuration of at least some of the plurality of environmental control devices. For at least some embodiments, the information includes a switch identification, and button activate information.

As described, each of the lighting devices receives a configuration control from the central server. For an embodiment, the central server receiving an input control from a system operator that provides adaptive control of the operating configuration of each of the lighting devices. That is, the system operator can control the operation of each of the lighting fixtures by providing the input control to the central server. The central server configures each of the lighting devices accordingly. However, for another embodiment, the central server monitors or receives monitoring information of occupancy behavior. Further, the operating configuration of each of the lighting devices is adaptively controllable based on the occupancy behavior.

For at least some embodiments, the wireless switch toggles through N states as controlled by physical activation of the wireless switch. For at least some embodiments, each of the plurality of lighting devices includes M scenes, wherein M is less than N, and wherein the plurality of lighting devices are synchronized to each other by selecting a present state of each of the plurality of lighting devices to be J mod M, wherein J is a one of the N possible states of the wireless switch.

As previously described, the operating configurations determine which of the lighting devices respond to the information and how each lighting device responds to the information. Note the wireless switches undergo no new configuration.

For at least some embodiments, the wireless switch further includes a temperature sensor, and wherein the wireless broadcast further includes temperature information at the wireless switch. For at least some embodiments, the wireless switch reports its measured temperature to the central controller. The temperature reporting can be useful for safety (fire) of a structure that includes the described systems, apparatuses and methods.

For at least some embodiments, the at least some of the plurality of lighting devices each receive the temperature information, and calibrate themselves based on the received temperature information of the wireless switch, and temperature information at the lighting device. Again, the temperature reporting can be useful for safety (fire) of a structure that includes the described systems, apparatuses and methods. For example, upon sensing a threshold temperature that suggests an emergency condition, the lighting devices can trigger themselves to go into an emergency state that include high-light levels, blinking lights, or provide indications as to where exists are located.

Figure 5:
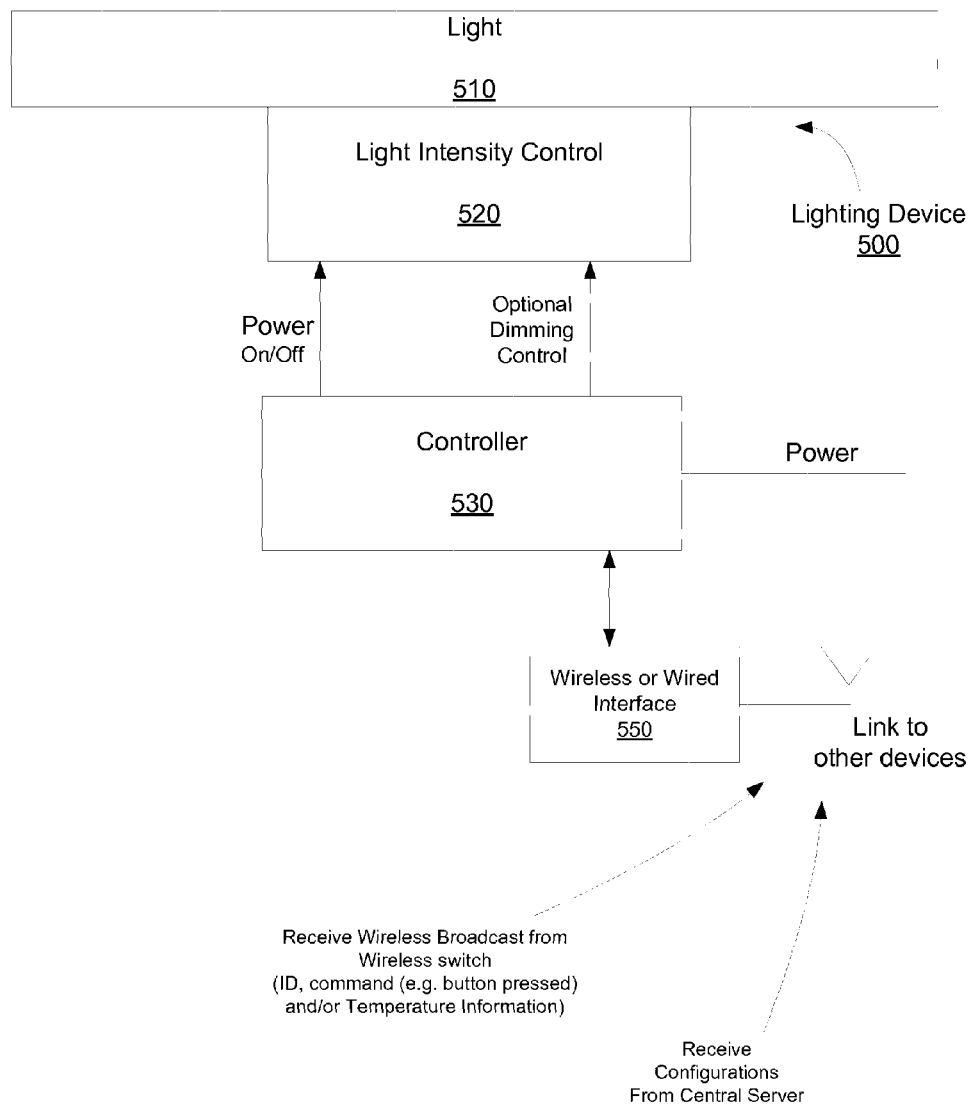
FIG. 5 shows a block diagram of a lighting device (fixture), according to an embodiment.

FIG. 5 shows a block diagram of a lighting device (fixture), according to an embodiment. As shown, this embodiment includes a light 510, a light intensity controller 520, a controller 530, and a communications interface 550. The intensity of light emitted from the light is controlled by the light intensity controller 520 which can be of different forms depending, for example, if the light 510 is an LED (light emitting diode) or florescent light.

For at least some embodiments, the controller 530 is operative to communicate with external devices (such as, receive one-way broadcasts from the wireless switch, or receive configurations from the central server) through the communications interface 550. For an embodiment, the communications interface 550 includes a wireless communication interface. The one-way broadcasts from the wireless switch include information. For an embodiment, the information includes a wireless switch identification and a command. For an embodiment, the information includes temperature information that indicates a sensed or measured temperature at the wireless switch.

The controller 530 is further operative to receive commands and react accordingly.

Figure 6:
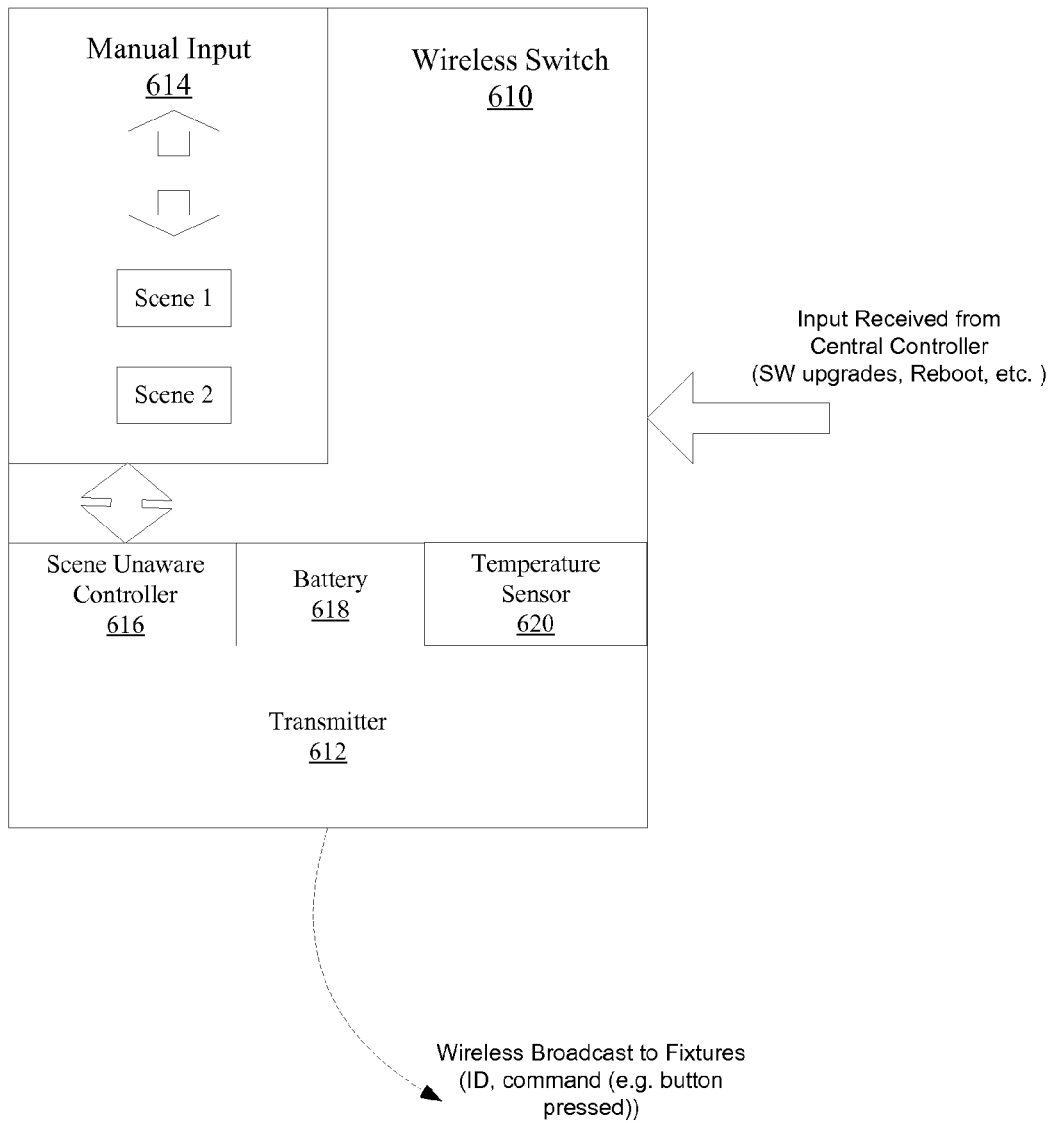
FIG. 6 shows a block diagram of a wireless switch, according to an embodiment.

FIG. 6 shows a block diagram of a wireless switch, according to an embodiment. The wireless switch 610 is operative to receive input control from a central control, which for an embodiment includes software upgrades etc. For an embodiment, the wireless switch includes buttons 614 allowing a manual input. For an embodiment, at least one of the buttons increments an internal counter each time the button is presses or activated. As such, the wireless switch is scene unaware and has no knowledge of the configurations of any of the devices, the wireless switch controls. The wireless switch 610 includes a scene unaware controller 616, which as stated, can be as simple as a counter that increments with each button push. A battery 618 power the wireless switch 610. A transmitter 612 provides one-way wireless broadcasts that the devices respond to based on the configurations of the devices. As stated, the broadcasts merely include a switch identifier and a command. In an implementation the command includes the button ID (identification) and a counter of the number of button pushes.

As shown, for at least some embodiments, the wireless switch includes a temperature sensor 620. The temperature sensor determines the temperature at the location of the wireless switch. In some situations, the wireless switch is located at a lower elevation as the devices the wireless switch is controlling. The location of the switch may provide an indication of temperature users within a structure in which the wireless switch and the devices are located are being subjected to. The wireless switch can propagate (for example, by including the temperature information within the broadcast) the sensed temperature, thereby allowing devices that receive the broadcast to calibrate themselves by comparing the switch temperature with their own temperature.

Although specific embodiments have been described and illustrated, the described embodiments are not to be limited to the specific forms or arrangements of parts so described and illustrated. The embodiments are limited only by the appended claims.

What is claimed:

1. A lighting control system, comprising:
   a plurality of lighting devices;
   a central server, wherein the central server communicates with each of the plurality of lighting devices, and controls an operating configuration of each of the lighting devices; and
   a switch, wherein the switch communicates with at least some of the plurality of lighting devices, wherein the communication includes information, and wherein the at least some of the plurality of lighting devices respond to the information of the communication based on the operating configuration of the at least some of the plurality of lighting devices, wherein the switch includes a wireless switch; wherein
   the wireless switch toggles through N states as controlled by physical activation of the wireless switch, and wherein each of the plurality of lighting devices includes M scenes, wherein M is less than N, wherein M is greater than one, and wherein the plurality of lighting devices are synchronized to each other by selecting a present state of each of the plurality of lighting devices to be J mod M, wherein J is one of the N possible states of the wireless switch.

2. The system of claim 1, wherein the communication includes a wireless broadcast, and the information includes a switch identification, and button activate information.

3. The system of claim 1, further comprising at least one of the plurality of lighting devices receiving the information and re-broadcasting the information to the central server or another lighting device.

4. The system of claim 2, wherein the wireless switch further comprises a temperature sensor, and wherein the wireless broadcast further includes temperature information at the wireless switch.

5. The system of claim 4, wherein the at least some of the plurality of lighting devices each receive the temperature information, and calibrate themselves based on the received temperature information of the wireless switch, and temperature information at the lighting device.

6. The system of claim 1, wherein the wireless switch includes a scene unaware operation, thereby allowing the wireless switch to deep-sleep and wakeup upon physical activation.

7. The system of claim 1, wherein the central server receives an input control from a system operator that provides adaptive control of the operating configuration of each of the lighting devices.

8. The system of claim 1, further comprising the central server monitoring or the central server receiving monitoring information of occupancy behavior, wherein the operating configuration of each of the lighting devices is adaptively controllable based on the occupancy behavior.

9. The system of claim 1, wherein the operating configurations determine which of the lighting devices respond to the information and how each lighting device responds to the information.

10. A method of controlling lighting of a structure, comprising:
    communicating, by a central server, with each of a plurality of lighting devices, wherein the communication provides control of an operating configuration of each of the lighting devices; and
    communicating, by a switch, with at least some of the plurality of lighting devices, wherein the communication includes information, and wherein the at least some of the plurality of lighting devices respond to the information based on the operating configuration of the at least some of the plurality of lighting devices, wherein the switch includes a wireless switch; wherein
    the wireless switch toggles through N states as controlled by physical activation of the wireless switch, and wherein each of the plurality of lighting devices includes M scenes wherein M is less than N wherein M is greater than one, and wherein the plurality of lighting devices are synchronized to each other by selecting a present state of each of the plurality of lighting devices to be J mod M, wherein J is a one of the N possible states of the wireless switch.

11. The method of claim 10, wherein the communication includes a wireless broadcast, and the information includes a switch identification, and button activate information.

12. The method of claim 10, further comprising sensing a temperature at the wireless switch, wherein the wireless broadcast further includes temperature information at the wireless switch, the at least some of the plurality of lighting devices each receiving the temperature information, and calibrating themselves based on the received temperature information of the wireless switch, and temperature information at the lighting device.

13. The method of claim 10, further comprising the central server receiving an input control from a system operator that provides adaptive control of the operating configuration of each of the lighting devices.

14. The method of claim 10, further comprising the central server monitoring or receiving monitoring information of occupancy behavior, wherein the operating configuration of each of the lighting devices is adaptively controllable based on the occupancy behavior.

15. The method of claim 10, wherein the operating configurations determine which of the lighting devices respond to the information and how each lighting device responds to the information.

16. An environmental control system, comprising:
    a plurality of environmental control devices;
    a central server, wherein the central server communicates with each of the plurality of environmental control devices, and controls an operating configuration of each of the environmental control devices; and
    a wireless switch, wherein the wireless switch communicates with at least some of the plurality of environmental control devices through a wireless broadcast, wherein the wireless broadcast includes information, and wherein the at least some of the plurality of environmental control devices respond to the information of the wireless broadcast based on the operating configuration of the at least some of the plurality of environmental control devices; wherein
    the wireless switch toggles through N states as controlled by physical activation of the wireless switch, and wherein each of the plurality of lighting devices includes M scenes, wherein M is less than N, wherein M is greater than one, and wherein the plurality of lighting devices are synchronized to each other by selecting a present state of each of the plurality of lighting devices to be J mod M, wherein J is a one of the N possible states of the wireless switch.

17. The system of claim 16, wherein the wireless switch further comprises a temperature sensor, wherein the wireless broadcast further includes temperature information at the wireless switch, and wherein the at least some of the plurality of lighting devices each receive the temperature information, and calibrate themselves based on the received temperature information of the wireless switch, and temperature information at the lighting device.

18. The system of claim 16, wherein the environmental control devices comprise at least one of a light fixture, ASC (air system control), HVAC (heating, ventilation, and air conditioning), and a fan.

19. The system of claim 16, wherein the central server receives an input control from a system operator that provides adaptive control of the operating configuration of each of the environmental control devices.

20. The system of claim 16, further comprising the central server monitoring or the central server receiving monitoring information of occupancy behavior, wherein the operating configuration of each of the environmental control devices is adaptively controllable based on the occupancy behavior.

21. The system of claim 16, wherein the operating configurations determine which of the environmental control devices respond to the information and how each environmental control device responds to the information.

\* \* \* \* \*